United States Patent [19]

Bigarella

[11] 4,129,130
[45] Dec. 12, 1978

[54] VIAL-SYRINGE

[76] Inventor: Federico Bigarella, Via S.Carlo, 32-Segrate (Milano), Italy

[21] Appl. No.: 660,424

[22] Filed: Feb. 23, 1976

[30] Foreign Application Priority Data

Nov. 5, 1975 [CH] Switzerland .................. 14312/75

[51] Int. Cl.² ............................................. A61M 5/00
[52] U.S. Cl. ................................................. 128/218 P
[58] Field of Search ........ 128/218 NV, 218 N, 218 P, 128/218 D, 218 DA, 218 R, 221, 215, 216, 234

[56] References Cited

U.S. PATENT DOCUMENTS

| | | | |
|---|---|---|---|
| 3,013,557 | 12/1961 | Pallotta | 128/218 R |
| 3,406,686 | 10/1968 | Keller | 128/218 NV |
| 3,413,974 | 12/1968 | Cohen | 128/218 NV |
| 3,886,930 | 6/1975 | Ryan | 128/218 NV |
| 3,895,633 | 7/1975 | Bartner et al. | 128/218 NV |

FOREIGN PATENT DOCUMENTS 724671 2/1955 United Kingdom ............. 128/218 NV
867972 5/1961 United Kingdom ............. 128/218 NV

*Primary Examiner*—John D. Yasko
*Attorney, Agent, or Firm*—Michael J. Striker

[57] ABSTRACT

A vial-syringe and method for filling same is disclosed. The vial-syringe comprises a cylindrical container having on one side a narrow neck, preferably also of cylindrical configuration, forming a shoulder for a piston and guide for the operating stem of the piston. At its other end the container is closed by a membrane or diaphragm pierceable by a needle having opposite points or tips. The method comprises the steps of introducing the piston until reaching and abutting the zone where the container neck is provided, then filling up the container with a medicine or drug, and finally tight sealing the container by means of a membrane which is force fitted or secured by a metal cap.

1 Claim, 3 Drawing Figures

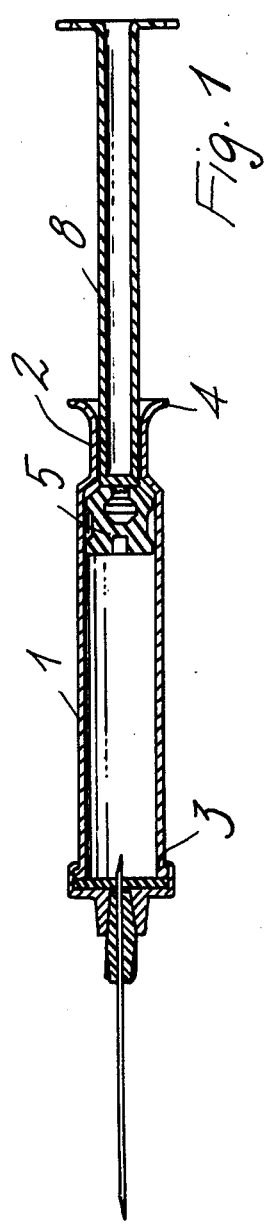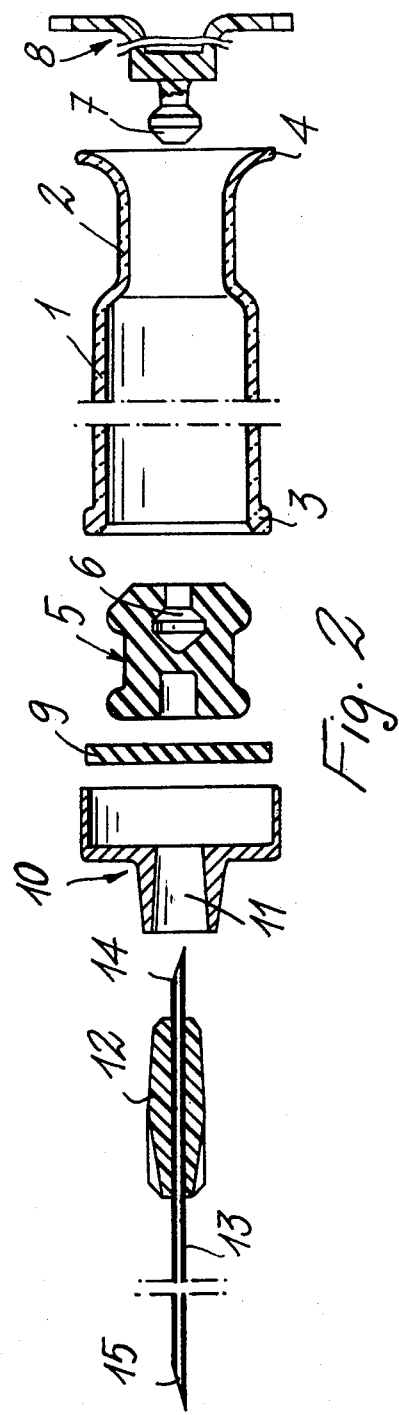

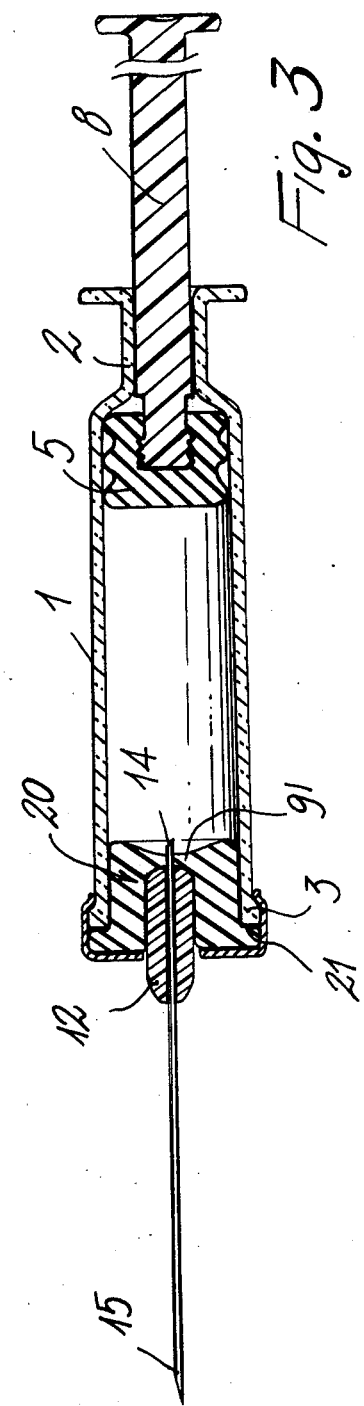

VIAL-SYRINGE

CROSS REFERENCE TO RELATED APPLICATION

This application is related to my copending patent application Ser. No. 660,423 filed 23 Feb. 1976.

BACKGROUND OF THE INVENTION

This invention relates to a vial-syringe which due to its essential characteristics can be subjected to any kind of sterilization, ensuring sealing, thorough sterility and great practicalness in use.

Such devices commonly referred to as vial-syringes, have been known for a long time and are of increasing wide spread use, being generally used for medecines or drugs, but particularly for serums and first aid products, and substantially comprising a container, preferably made of glass and on one side closed by a sealing piston and connected or connectable to a piston, so that when being used the container will act as the syringe cylinder. Prior art vial-syringes suffer from several shortcomings, particularly as to possibilities of prewashing the empty vials, sterilizing such empty vials and sterilizing the vials after filling up. In other known types of vial-syringes, wherein these shortcomings are of minor importance or magnitude, sealing means are provided which rupture when being used, by the pressure exerted by the piston, with easily imaginable drawbacks of other nature.

SUMMARY OF THE INVENTION

In order to overcome the above mentioned disadvantages, the present invention proposes a vial-syringe, substantially comprising a cylindrical container having at one end a narrow neck also of cylindrical configuration, into which container and prior to the filling up thereof a piston is introduced, this piston stopping at the shoulder formed by the narrow neck and following the filling up operation, the container is closed at the widest end by a resilient membrane interposed between the container and a ring nut receiving a needle having opposite points or tips, a seat being provided in the piston for engaging a head of a piston or plunger that can be slipped into the minor diameter portion of the container.

This invention is also concerned with a method for filling up the vial-syringe according to the invention, the method being characterized in that a previously washed, two-inlet container has a piston introduced thereinto until it abuts the narrow neck zone of the container. The container is then fitted and finally the container is closed at the open end by a ring nut through the intermediary of a resilient membrane.

BRIEF DESCRIPTION OF THE DRAWING

The present invention can be more clearly understood from the following detailed description given by mere way of unrestrictive example, reference being particularly had to the figures of the accompanying drawings, in which:

FIG. 1 is a sectional view of a vial-syringe according to the invention;

FIG. 2 is an exploded sectional view showing the component parts of the vial-syringe; and FIG. 3 is a sectional view showing a possible modified form according to the invention.

A vial-syringe according to the invention substantially comprises a cylindrical container 1 made of glass or plastic material, on one side having a narrow neck 2 also of cylindrical configuration. At the two opposite ends provision is made for rims designated by 3 and 4 respectively, preferably of the same outer diameter to facilitate handling and transport of the containers during the various filling up, processing and packaging operations.

According to the invention, a piston is also provided and designated as a whole at 5, the piston being preferably made of yieldable material and fitted with two or more external bands for ensuring liquid tight sealing on the inner surface of the cylindrical major diameter zone of the container 1. A slot 6 of undercut or threaded configuration is provided in the plunger 5 for accomodating a corresponding head of a piston designated as a whole at 8.

The vial-syringe is completed by a resilient membrane 9 which is secured at rim 3 by means of a ring nut, designated as a whole at 10, force fitted over the rim and having an aperture 11, preferably of a frusto-conical shape, for forcibly accomodating a plug 2, the latter being mounted on a needle 13 having opposite points or tips designated at 14 and 15, respectively.

According to the invention, filling up operation is carried out as follows.

Into a thoroughly washed and/or sterilized container, the operation being facilitated by the provision of two opposite open inlets, piston 5 is introduced from mouth or rim 3 until reaching the shoulder defined by the narrow neck 2, then the container is filled with the medecine or drug and ring nut 10 is fitted on with interposition of the resilient membrane 9.

As readily apparent from the foregoing, a vial-syringe is thus obtained, the vial-syringe being closed on one side by piston 5 and on the other side by membrane 9, thoroughly tightly sealed and sterilized, the packaging of which is particularly simple and rational.

At the time of use, it is only necessary to insert plug 12 into the seat 11 of ring nut 10, so that the needle point or tip 14 pierces and through the membrane 9. The head 7 of plunger 8 for the seat 6 of piston 5 is inserted on the other side to obtain the "syringe" configuration shown in FIG. 1. Now, by pressing on the plunger 8 and grasping the rim 4 of container 1, piston 5 is operated to drive the contained liquid through needle 13. It should be noted that due to removability thereof both piston 8 and needle 13 can be used for a multiplicity of vial-syringes and accordingly packages can be made available as provided with a multiplicity of vial-syringes and a single piston and needle. It should also be noted that the cylindrical portion 2 can act as a guide for plunger 8, so as to prevent any unwanted coating or twisting between the piston and cylinder.

In the embodiment shown in FIG. 3, ring nut 10 is replaced by a plug of yieldable material, designated as a whole at 20, simultaneouly accomplishing the function of a seating for the needle drum 12 and membrane 9' intended to be pierced by the needle end 14. According to this embodiment, the plug 20 partially inserted into the container is held on by a metal membrane 21 on the above mentioned container rim 3.

Although only two embodiments of the invention have been described and shown, those skilled in the art can now readily devise many modifications and changes, all of which are to be considered as within the scope of the present invention.

What is claimed is:

1. A syringe, comprising an elongated container having a longitudinal axis, a wall bounding the interior of said container, a leading open end of a predetermined major diameter and a substantially cylindrical trailing open end of a predetermined minor diameter smaller than the major diameter, said trailing end extending substantially parallel to the longitudinal axis of said container and provided at its open end with a rim projecting outwardly and substantially normal to said longitudinal axis of said container, and having an outside diameter substantially equal to the major diameter of the leading end, thereby bounding a circumferential recess on an outside surface of the wall for receiving a user's fingers therein, said recess having a front end face directed towards said leading open end of the predetermined major diameter and rear end face directed towards said rim of the outside diameter substantially equal to the major diameter to thereby eliminate the user's fingers slipping along and from said barrel container in either directions; an elastomeric piston axially slidable in said container and having an outside diameter equal substantially to said major diameter, said piston being formed with a recess open axially toward said other end whereby said piston can be introduced into said container through said one end; an elongated plunger extending axially into said container through said narrow neck and having an end formation snugly engaged in said recess of said piston; a pierceable membrane sealingly covering said one end; a cap force fitted over said membrane at said one end and securing said membrane tightly in place thereon, said cap forming seat open axially away from said container; a hollow needle having a pair of oppositely directed pointed fingers; and a plug surrounding said needle intermediate said tips thereof and snugly receivable in said seat with one of said tips engaging through said membrane into said body portion.

* * * * *